(12) United States Patent
Carr

(10) Patent No.: US 6,587,732 B1
(45) Date of Patent: Jul. 1, 2003

(54) HEAT TREATMENT FOR VIRAL INACTIVATION

(76) Inventor: Kenneth L. Carr, 30 Woodside Rd., Harvard, MA (US) 01451

( * ) Notice: Subject to any disclaimer, the term of this patent is extended or adjusted under 35 U.S.C. 154(b) by 1022 days.

(21) Appl. No.: 08/980,536

(22) Filed: Dec. 1, 1997

Related U.S. Application Data

(63) Continuation of application No. 08/650,422, filed on May 20, 1996, now abandoned, which is a continuation of application No. 08/312,310, filed on Sep. 26, 1994, now abandoned, which is a continuation-in-part of application No. 08/124,928, filed on Sep. 21, 1993, now abandoned, and a continuation-in-part of application No. 08/142,577, filed on Oct. 26, 1993, now abandoned, which is a continuation of application No. 07/808,854, filed on Dec. 16, 1991, now abandoned, which is a continuation of application No. 07/067,626, filed on Jun. 26, 1987, now Pat. No. 5,073,167.

(51) Int. Cl.[7] .............................................. A61B 18/18
(52) U.S. Cl. ...................... 607/102; 128/898; 219/679; 219/687; 219/692; 219/710
(58) Field of Search ................................ 219/678, 679, 219/687, 691, 692, 702, 704, 710, 762; 606/27–31; 607/99–106; 600/549; 128/898

(56) References Cited

U.S. PATENT DOCUMENTS 4,309,592 A * 1/1982 Le Boeuf .................... 607/106
4,715,727 A * 12/1987 Carr ............................ 600/549

OTHER PUBLICATIONS

"High–Temperature Short–Time Heat Inactivation of HIV and Other Viruses in Human Blood Plasma" by Charm et al; 1992 Charm Bioengineering Inc pp 12–20.*

* cited by examiner

*Primary Examiner*—David M. Shay
(74) *Attorney, Agent, or Firm*—Cesari and McKenna, LLP

(57) ABSTRACT

Heat treatment apparatus for inactivating viruses in blood products includes a series of tubing coils with connectors at the opposite ends of the series for connecting the tubing to a blood product source and a blood product destination. The apparatus also includes a microwave heating chamber arranged to receive the first coil of the series and a cooling chamber adapted to receive the second coil of the series. Microwave energy is supplied to the heating chamber for heating the blood product as it flows along the first coil from an initial temperature to an elevated temperature and the cooling chamber is cooled so that the blood product in the second coil is cooled to a selected temperature appreciably below the elevated temperature. A radiometer circuit is provided for monitoring the temperatures of the blood product in the first and second coils to produce first and second temperature signals in response thereto. A controller responds to these temperature signals by controlling the energy producing means to impart a selected time/temperature profile to the blood product flowing through the tubing and to deliver that product at a selected delivery temperature. A third coil and a second heating chamber may be provided to heat the blood product to the delivery temperature following the cooling thereof.

3 Claims, 1 Drawing Sheet

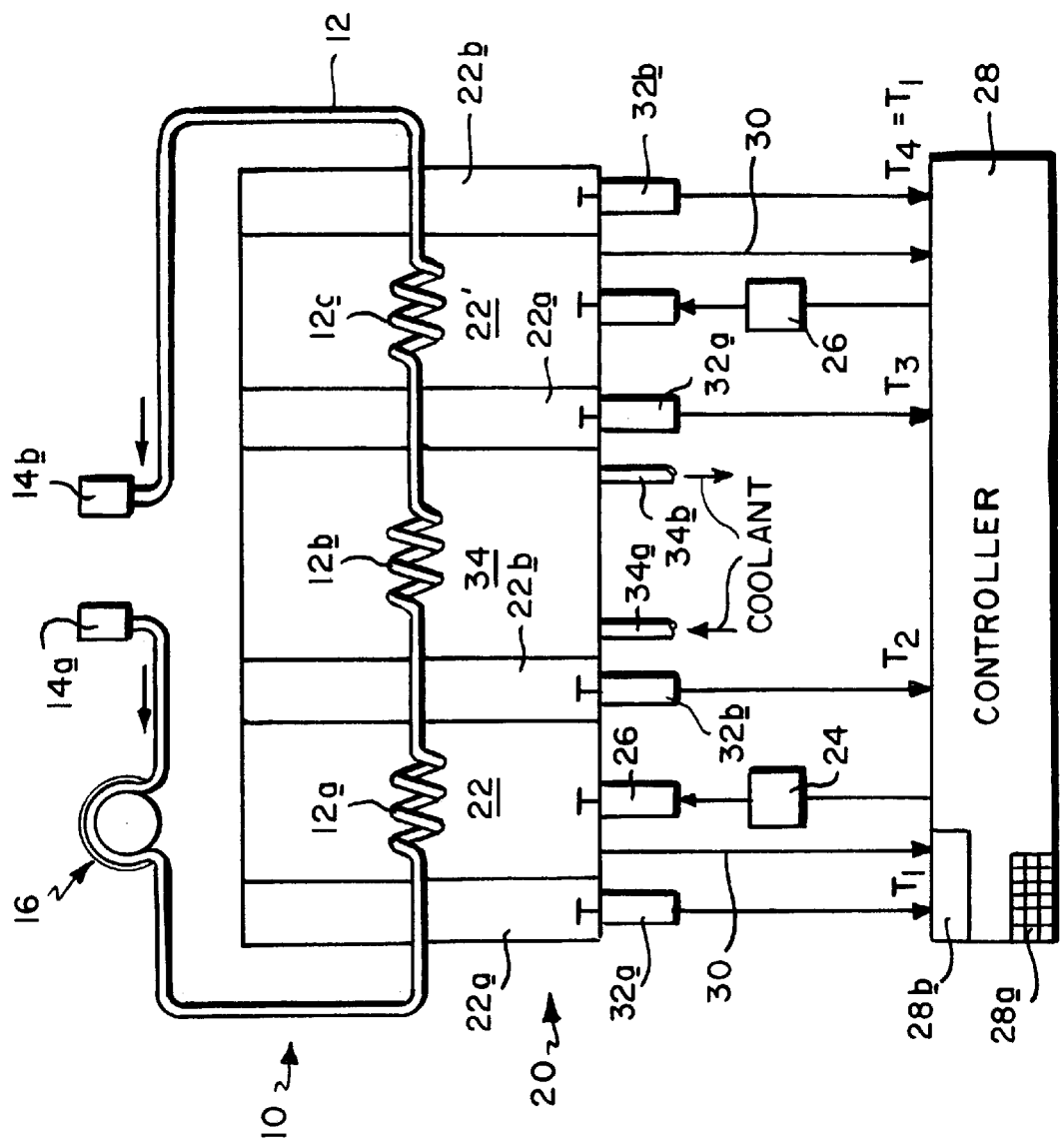

HEAT TREATMENT FOR VIRAL INACTIVATION

RELATED APPLICATIONS

This application is a continuation of Ser. No. 08/650,422, filed May 20, 1996 now abandoned, the contents of which is hereby incorporated herein by reference, which is a continuation of Ser. No. 08/312,310, filed Sep. 26, 1994 now abandoned, which is a continuation-in-part of Ser. No. 08/124,928, filed Sep. 21, 1993 and Ser. No. 08/142,577, filed Oct. 26, 1993, both now abandoned, the former of which is a continuation of Ser. No. 07/808,854, filed Dec. 16, 1991, now abandoned, which is a continuation of Ser. No. 07/067,626, filed Jun. 26, 1987, now U.S. Pat. No. 5,073,167.

FIELD OF THE INVENTION

This invention relates to the inactivation of viruses in blood products. It relates more particularly to a method and apparatus for inactivating viruses in blood products through the use of high temperature short time heating (HTST) of those products.

BACKGROUND OF THE INVENTION

Currently in the United States, about 3 to 4 milling people receive blood transfusions each year, averaging 3.5 units per person. As is well known, serious reactions can occur at the time of transfusion, including the transmission of blood born infection such as hepatitis, syphilis and the HIV virus. Despite the existence of tests for such infections and improved donor selection and screening procedures, each year many people acquire viral illnesses from transfusions of blood products such as whole blood, red blood cells, plasma, platelets and leukocyte concentrates.

In an effort to alleviate this problem, it has been proposed to subject the blood products at the time of "manufacture" to HTST heating similar to that practiced in sterilization and pasteurization processes to achieve substantially complete destruction of pathogens in the blood while maintaining cellular viability. The trouble is, that the HTST systems currently used in sterilization and pasteurization processes are not able to achieve the time-temperature relationship that produces a sufficient reduction of contaminating viruses while preserving biological activity in the blood products.

Also, the paper entitled High-Temperature Short-Time Heat Inactivation of HIV and Other Viruses In Human Blood Plasma, by S. E. Charm, et al., published in Vox Sang, 1992; 62:12–20, hereby incorporated by reference herein, discloses an HTST system specifically designed to inactivate HIV and other viruses in human blood plasma. However, the system described there is limited to heating only a 10 ml bolus of fluid. Still, the data obtained by the authors of that article are useful in establishing the feasibility of using microwave heating to deactivate viruses in blood plasma and indicate that a high-level of virus inactivation with modest to no changes in plasma components can be achieved with microwave exposure times of 0.006 second at a temperature between 75° C. and 78° C. With that temperature range, various viruses including HIV were reduced to less than the lowest detectable amount.

However, the prior HTST systems, including the one described in the above paper, are disadvantaged in that they are basically batch systems. Some take a relatively long time to reach the process temperature; some require a relatively long hold up time at the process temperature and some take a relatively long time to cool the process fluid to a non-destructive temperature. For example, one HTST system of which we are aware marketed by Alfa Laval under the name Sterimedia Mini and referred to in the above paper has a hold time of about 2 to 4 seconds or more and a hold up volume of 1.5 liters, making it necessary to waste a large volume of product during processing.

SUMMARY OF THE INVENTION

Accordingly, this invention aims to provide an improved method of inactivating viruses in blood products while maintaining cellular function.

Another object of the invention is to provide a method of inactivating viruses in blood products by high-temperature short-time heating of the blood products on a continuous in-line basis.

A further object of the invention is to provide an HTST heating method which overcomes limitations of the prior processes by delivering microwave heating to a well defined in-line flowing pathway of a blood product in a rapid, uniform and controlled manner.

Still another object of the invention is to provide a unique HTST heating technique that allows exposure of blood products to uniform microwave heating energy for the purpose of virus deactivation as the contaminated fluid flows in-line through a microwave heating chamber and then through a cooling chamber.

Yet another object of the invention is to provide a high-temperature short-time microwave heating method which permits the shaping of the heating time and temperature parameters to provide heat destruction of virus activity while maintaining the functional constituency of the otherwise heat-sensitive blood products.

A further object of the invention is to provide apparatus for heat treating blood products to achieve viral inactivation and having one or more of the above advantages.

Other objects will, in part, be obvious and will, in part, appear hereinafter.

The invention accordingly comprises the several steps and the relation of one or more of such steps with respect to each of the others, and the apparatus embodying the features of construction, combination of elements and arrangement of parts which are adapted to effect such steps all as exemplified in the following detailed description, and the scope of the invention will be indicated in the claims.

Briefly, our HTST system for achieving viral inactivation in blood products is an in-line system that processes the blood products on a continuous basis and in a rapid, uniform and closely controlled manner.

A blood product, e.g., whole blood, plasma, etc. is flowed through a series of at least two, and preferably three, coils, each of which has a small priming volume, e.g., 4–5 ml. The first coil is situated in a microwave heating chamber, the second coil reposes in a cooling chamber and the third coil (if present) is positioned in a second microwave heating chamber that may be similar to the first such chamber.

In the first coil, the blood product is exposed to uniform microwave energy present in the first chamber which heats the product to a temperature sufficient to deactivate any viruses present in the product. The heated product then flow through the second coil in the cooling chamber where it is immediately cooled to a lower delivery temperature.

Using non-invasive radiometric temperature sensors, the temperature profile along the product heating/cooling pathway is obtained and used to control the heating chamber to maintain a uniform product delivery temperature despite variations of fluid parameters such as flow rate and inlet temperature. In this way, the product heating time and temperature parameters may be controlled carefully to allow complete destruction of virus activity in the blood product while maintaining the viability of the product.

As noted above, in many cases it is desirable to route the blood product through a third coil positioned in a second microwave heating chamber. This allows the product to be cooled in the cooling chamber to a temperature below the desired delivery temperature and then be heated somewhat so that the target temperature is approached from below. This allows optimum control over the product delivery temperature.

Preferably, the coils are provided as single use disposable cartridges with conventional connectors at opposite ends of the tubing runs to enable the cartridges to be connected together and to the blood product source and destination. Alternatively, the two or three coils may be formed together as a single cartridge unit. The source and destination may be standard blood bags when processing stored blood products or cannulae if a patient's blood is being processed extracorporally in a manner similar to dialysis.

The cartridges are designed to plug into receptacles in the heating and cooling chambers so that they are automatically positioned at the proper locations in those chambers as described in commonly owned U.S. Pat. No. 5,073,167 and pending application Ser. No. 08/142,577, the contents of which are hereby incorporated by reference herein.

BRIEF DESCRIPTION OF THE DRAWING

For a fuller understanding of the nature and objects of the invention, reference should be had to the following detailed description taken in connection with the accompanying drawing which is a schematic view of a treatment apparatus incorporating the invention.

DETAILED DESCRIPTION OF THE PREFERRED EMBODIMENT

In accordance with the present invention, a continuously moving column of a blood product from a patient or other source is rapidly heated in a microwave heating chamber to a temperature high enough to provide heat destruction of virus activity in the product and then the moving liquid is immediately cooled in an in-line cooling chamber to a non-destructive delivery temperature, e.g., body temperature (about 37° C.). Preferably, in some cases, the liquid product is cooled in the cooling chamber below the selected delivery temperature and then routed to another in-line microwave heating chamber which heats the product precisely to the desired delivery temperature. In this way, the delivery temperature is approached from below for optimum accuracy.

The blood product is flowed through the successive chambers through IV tubing whose I.D. is preferably quite small, e.g. 0.096 in., with respect to the wavelength of the microwave heating frequency thereby ensuring uniform heating of the liquid which is in constant motion through the tubing. Preferably also, the tubing is formed as a cartridge unit with a series of two (or three) coils which may be positioned in the two (or three) chambers present in the apparatus. Further in accordance with the present invention, means are provided for monitoring the temperature of the moving liquid as it enters and leaves the various chambers utilizing non-invasive radiometry with detection occurring at microwave frequencies. This enables noninvasive measurements at is depth to occur while the liquid is in motion through the tubing. The measured differential temperatures are then used to determine the power level required for heating in the first (and, if present, the second) heating chamber.

Using the in-line high temperature short time heating method described herein, a time/temperature profile may be produced in the moving column of blood product to provide maximum heat destruction of virus activity while maintaining the functional constituency of the blood product and product delivery at the proper delivery temperature.

Referring to the drawing figure, the blood product is flowed through a cartridge unit shown generally at 10. The illustrated cartridge unit includes dielectric tubing 12 with three tubing coils 12a, 12b and 12c in series. Actually, the cartridge unit 10 may consist of three of the cartridges depicted in the above pending application connected in series or it may be formed with a continuous length of tubing 12. In either event, the tubing ends at the opposite ends of the series are provided with conventional connectors 14a and 14b to enable the cartridge unit 10 to be connected to a blood product source and destination. For example, connector 14a may be connected to a blood bag full of blood product and connector 14b may be coupled to an empty blood bag or to a cannula inserted into a patient. If desired, a non-invasive flow regulator or paristoltic pump 16 may be provided to control the flow of blood product through tubing 12. Preferably, the blood product should flow through the tubing at a substantially constant velocity.

Cartridge unit 10 is arranged to be used in conjunction with the heating/cooling apparatus shown generally at 20. Apparatus 20 includes a microwave heating chamber 22 having an inlet waveguide 22a and an outlet waveguide 22b and an aperture for receiving the cartridge unit coil 12a. Microwave energy from a microwave transmitter 24 is coupled to heating chamber 22 by way of a standard launch or probe 26 that projects into chamber 22. Transmitter 24 may be controlled by a controller 28 having a control panel or keyboard 28a.

The temperature of the liquid flowing through the tubing coil 12a in chamber 22 is monitored radiometrically using a sensing probe (not shown) similar to probe 26 which is connected by a coaxial conductor 30 to a radiometer 28b in controller 28. Similar sensing probes 32a and 32b are present in the inlet and outlet waveguides 22a and 22b to monitor the temperature of the liquid in tubing 12 entering and leaving chamber 22. The controller 28 responds to the temperature measurements provided by the various sensing probes to control the power of the microwave energy injected into chamber 22 via launch probe 26 so as to raise the temperature of the liquid flowing through the tubing coil 12a from an initial value $T_1$ which may be, e.g., room temperature, to a selected value $T_2$ sufficient to inactivate viruses in the blood product, e.g., 77° C. Since the construction and operation of chamber 22, with its probes, radiometric circuitry and controller, is described in detail in the above U.S. Pat. No. 5,073,167, we will not describe it again here.

Apparatus 20 also includes a cooling chamber 34 with an aperture for receiving the tubing coil 12b. Chamber 34 is provided with an inlet tube 34a and an outlet tube 34b by which a coolant may be circulated through chamber 34 in order to rapidly, e.g., 1 second or less, cool the blood product exiting chamber 22 to a non-destructive temperature $T_3$ which may be somewhat below the ultimate delivery temperature, e.g., to 30° C.

The illustrated cartridge unit 10 has, in addition, a third tubing coil 12c which is adapted to be received in a third chamber 22' of apparatus 20. Chamber 22' is another microwave heating chamber which may be substantially identical to chamber 22. Accordingly, its parts have the same numeric identifiers as the corresponding parts in chamber 22. Its function is to controlledly heat the column of liquid flowing through tubing 12 after the liquid has been cooled in chamber 34. Using this 3-stage apparatus, the blood product, having been overcooled in chamber 34, may be heated in chamber 22' so that when the product leaves apparatus 20 it has a desired delivery temperature $T_4$ which may be the same as the initial temperature $T_1$. Allowing overshoot during cooling provides more rapid cooling and, in turn, better control of the duration of the short-line heating to reach the desired delivery temperature.

If the second heating chamber 22' is not used, a waveguide similar to waveguide 22a with a sensing probe 32a connected to radiometer 28b should be provided to radiometrically measure the temperature of the blood product exiting cooling chamber 34. In this event, the temperature $T_3$ of the liquid as it leaves chamber 34 should be the desired delivery temperature.

During operation of the apparatus, the blood product is flowed through cartridge unit 10 at a predetermined velocity. That velocity and the tubing 12 dimensions determine the residence time of the blood product in the heating chamber 22. Thus, by presetting those parameters and controlling the power of the microwave energy in chamber 22, the time/temperature profile of the moving column of liquid may be shaped to produce viral inactivation without undue cell damage.

The above described in-line cooling of the blood product following heating allows the product to be heated to temperatures assumed prohibited heretofore because, in the present apparatus, the heat exposure will be determined solely by the microwave power applied in chamber 22 to the liquid and the liquid flow rate, bearing in mind that only a small amount of liquid is heated at any given moment in the cartridge coil 12a in chamber 22. Because such a small blood product volume is envolved, the warm-up time is very short and there is essentially no hold up time because the product is always moving through the apparatus. Finally, due to the nature of the apparatus, the blood product is subjected to uniform and closely controlled heating for the reasons stated in the above patent.

It will be thus be seen that the objects set forth above, among those made apparent from the preceding description, are efficiently attained. Also, certain changes may be made in carrying out the above method and in the construction set forth without departing from the scope of the invention. For example, it is also known that heat acts as a catalyst to chemical reactions and that heat enhances the ability of certain drugs to destroy viruses. Therefore, during drug therapy, blood products can be subjected to controlled heating in accordance with this invention to increase the efficacy of that therapy. Therefore, it is intended that all matter contained in the above description or shown in the accompanying drawing shall be interpreted as illustrative and not in a limiting sense.

It is also to be understood that the following claims are intended to cover all of the generic and specific features of the invention described herein.

What is claimed is:

1. A heat treatment method for achieving viral inactivation in a blood product, said method comprising the steps of
   flowing a blood product at a selected flow rate along a length of small diameter tubing formed into a series of coils including a first coil, a second coil and a third coil;
   applying electromagnetic energy to said first coil to heat the blood product flowing therein from an initial temperature to a selected elevated temperature sufficient for viral inactivation;
   cooling the second coil to rapidly cool the blood product flowing therein;
   radiometrically monitoring the temperature of the blood product in said first and second coils to produce first and second temperature signals;
   controlling the flowing, applying and/or cooling steps in response to said first and second temperature signals to impart a selected time/temperature profile to the blood product flowing in the tubing and to deliver the blood product to the third coil at a selected temperature somewhat below body temperature;
   applying electromagnetic energy to the third coil and the blood product flowing therein;
   radiometrically monitoring the temperature of the blood product in the third coil and producing a third temperature signal in response thereto, and
   controlling the energy applied to the third coil in response to the third temperature signal so that the blood product flowing in the third coil is reheated to body temperature whereby the body temperature is approached from below.

2. Heat treatment apparatus for achieving viral inactivation in a blood product, said apparatus comprising;
   a length of small diameter dielectric tubing having opposite ends and formed into a series of coils including a first coil, a second coil and a third coil;
   a first connector mounted to one end of the tubing for connecting the tubing to a blood product source;
   a second connector mounted to the other end of the tubing for connecting the tubing to a blood product destination;
   flow means for flowing blood product from said source along said tubing at a selected flow rate;
   a first electromagnetic heating chamber enclosing said tubing, said chamber having an access opening receiving said first coil into said first heating chamber;
   energy producing means connected to said first heating chamber for providing electromagnetic energy to said first heating chamber to heat the blood product flowing in said first coil from an initial temperature to a selected elevated temperature sufficient for viral inactivation;
   a cooling chamber adjacent to said first heating chamber and enclosing said tubing, said cooling chamber having an access opening for receiving said second coil into said cooling chamber;
   cooling means connected to said cooling chamber for rapidly cooling the blood product flowing in the second coil;
   a second electromagnetic heating chamber adjacent to said cooling chamber and having an access opening for receiving said third coil into said second heating chamber;
   additional energy producing means connected to said second heating chamber for providing electromagnetic energy to said second heating chamber to heat the blood product flowing in said third coil;

means in said first and second heating chambers and said cooling chamber for radiometrically monitoring the temperatures of the blood product flowing in said first, second and third coils, respectively, and producing first, second and third temperature signals in response thereto, and control means connected to said monitoring means and responsive to the first and second temperature signals for controlling the flow means, energy producing means and/or cooling means to impart a selected time-temperature profile to the blood product flowing along the tubing and to deliver the blood product to the third coil at a selected temperature somewhat below body temperature, said control means also controlling the additional energy producing means so as to reheat the blood product flowing in the third coil to body temperature whereby the body temperature is approached from below.

3. The apparatus defined in claim 2 and further including means for radiometrically monitoring the temperature of the blood product entering and leaving said first coil and producing fourth and fifth electrical signals in response thereto, and means for radiometrically monitoring the temperature of the blood product entering and leaving said third coil and producing sixth and seventh electrical signals in response thereto, said control means responding to all of said temperature signals while controlling the energy producing means and the additional energy producing means.

* * * * *